(12) United States Patent
Fattaey

(10) Patent No.: US 6,391,630 B1
(45) Date of Patent: May 21, 2002

(54) PLASMIDS THAT ENCODE GREEN FLUORESCENT PROTEIN

(75) Inventor: Ali Fattaey, San Francisco, CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/260,420

(22) Filed: Mar. 1, 1999

Related U.S. Application Data

(63) Continuation of application No. 08/657,828, filed on May 31, 1996, now Pat. No. 5,876,711.

(51) Int. Cl.[7] .............................................. C12N 15/00
(52) U.S. Cl. ................ 435/320.1; 435/172.3; 435/252.3
(58) Field of Search ......................... 434/6; 435/320.1, 435/172.3, 252.3

(56) References Cited

PUBLICATIONS

Gudas et al (Carcinogenesis, 17:1417–1427), 1996.*
Badie et al (J. Neuro–oncology, 37:217–222), 1998.*
Chiarugi et al (Tumori, 84;517–520), 1998.*
Kyprianou et al (Anticancer Res., 18:897–905, 1998.*
Nakamura et al (Oncology Reports, 7:261–265), 2000.*
Xi et al (Clinical Cancer Res., 5:4224–4232), 1999.*
Tada et al (Cancer Res., 58:1793–1797), 1998.*
Proc. AACR, 38:A3622, 1997.*
Saito et al (Intl J. Radiation Oncology Biol. Phys., 38:623–631, 1997.*
Zellars et al (radiation Oncology Investigations, 5:43–49), 1997.*
Servoma et al (Cell Proliferation, 29:219–230), 1996.*
Slichenmyer et al (Cancer Res., 53:4164–4168), 1993.*
O'Connor et al (Cancer Res., 53:4776–4780), 1996.*

* cited by examiner

*Primary Examiner*—Susan Ungar
(74) *Attorney, Agent, or Firm*—Gregory Giotta

(57) ABSTRACT

Methods and compositions for determining the tumor suppressor status of cells are described, preferably as pertaining to the p53 status of tumor cells, and preferably in vivo using a recombinant construct consisting of a first polynucleotide sequence that encodes a reporter molecule and a second p53 binding polynucleotide sequence that is operably linked to the first polynucleotide sequence such that binding of p53 to the second polynucleotide sequence causes the expression of the reporter molecule which can be detected or quantified.

4 Claims, 5 Drawing Sheets

```
 11           20          30          40          50          60
  •            •           •           •           •           •
TAGCGCTACCGGACTCAGATCTCGAGCTCAAGCTTCGAATTCTGCAGTCGAC
 EcoA7 III         Bgl II      Sac I  Hind III    Pst I
                          Xho I  Ech 36 II   EcoR I      Sal I 70           80          90
       •            •           •          GFP →
  GGTACCGCGGGCCCGGGATCCACCGGTCGCCACC ATG GGT
  Kpn I    Apa I   BamH I  Age I
  Asp718 I  Bsp120 I
       Sac II    Xma I
                 Sma I
```

FIGURE 2

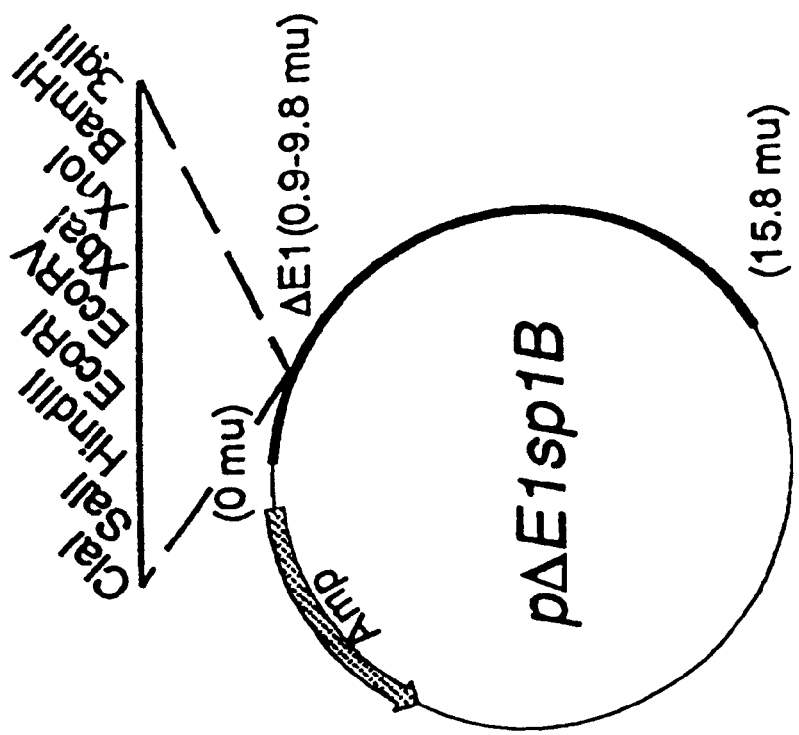
FIGURE 4
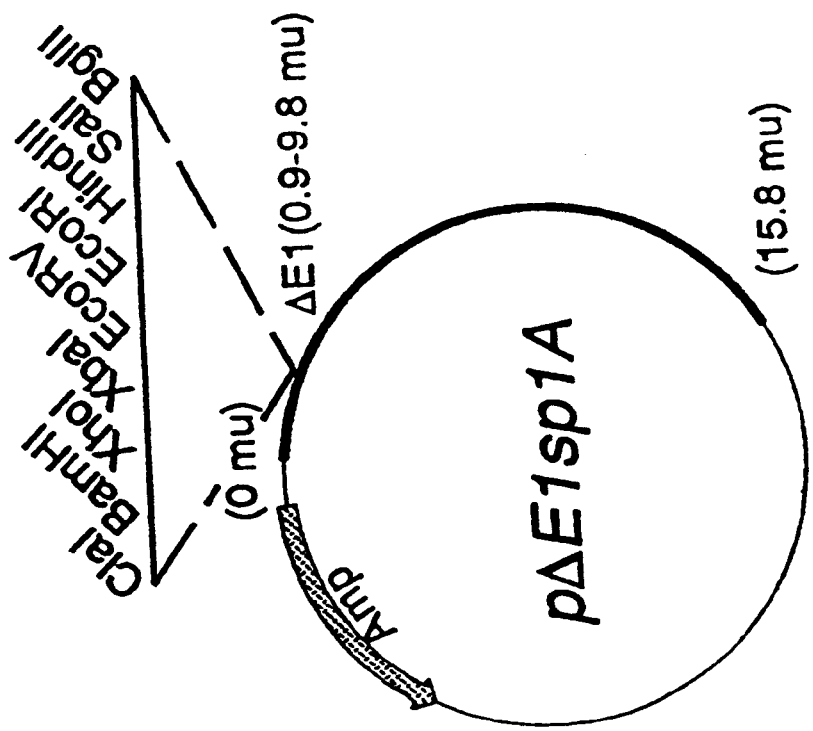

PLASMIDS THAT ENCODE GREEN FLUORESCENT PROTEIN

This application is a continuation of U.S. Pat. No. 08/657,828; filed May 31, 1996, now U.S. Pat. No. 5,876,711.

FIELD OF THE INVENTION

This invention relates to cancer, and particularly to diagnosing and treating tumors premised on the tumor suppressor status of cancer cells. The invention will have significant applications for cancer diagnosis and therapy.

BACKGROUND OF THE INVENTION

It has been known for some time that a variety of cancers are caused, at least in part, by mutations to certain normal genes, termed "proto-oncogenes." Proto-oncogenes are involved in regulating normal cell growth in ways that are only now beginning to be appreciated at the molecular level. The mutated proto-oncogenes, or cancer causing genes termed "oncogenes," disrupt normal cell growth which ultimately causes the death of the organism, if the cancer is not detected and treated in time.

During normal or cancer cell growth, proto-oncogenes or oncogenes, are counterbalanced by growth-regulating proteins which regulate or try to regulate the growth of normal or cancer cells, respectively. Such proteins are termed "tumor suppressor proteins." A number of such proteins are known.

A gene that encodes a tumor suppressor protein termed p53 is frequently mutated in a number of human cancers, and the inactivation of p53 is thought to be responsible for the genesis or progression of certain cancers (Nigro et al., 1989, Nature 342:705–708), including human colorectal carcinoma (Baker et al., 1989, Science 244:217–221), human lung cancer (Takahashi et al., 1989, Science 246:491–494; Iggo et al., 1990, Lancet 335:675–679), chronic myelogenous leukemia (Kelman et al., 1989, Proc. Natl. Acad. Sci. USA 86:6783–6787) and osteogenic sarcomas (Madsuda et al., 1987, Proc. Natl. Acad. Sci. USA 84:7716–7719). Tumor cells that exhibit p53 are more sensitive to radiation treatment than tumor cells that have little or no p53. Thus, knowledge of the p53 status of tumors has significant practical applications for aiding a physician in the selection of the most appropriate treatment modality.

Despite the strong experimental evidence supporting a role for p53 in tumorigenesis, there are currently only a few methods available for determining the presence of wild type or mutant p53 protein in mammalian cells. One widely used method involves time consuming DNA sequencing of the p53 gene itself. A limitation of this approach is that the presence of a normal p53 DNA sequence is not always an accurate predictor of the presence of functional p53 protein in the cells assayed since p53 function can be masked by binding of p53 protein to endogenous cellular or viral proteins (Momand, J. et al. (1992) Cell, 69:1237–1245; Oliner, J. D. et al. (1992) Nature, 358:80–83). Furthermore, this approach is both expensive to perform and time-consuming.

Another method used for determining the presence of wild type or mutant p53 involves the use of antibodies capable of distinguishing between these two forms of p53. However, this approach also has several limitations. Firstly, many of the mutations which arise in the p53 protein are point mutations and not all such mutations can be distinguished by a limited number of antibodies. Secondly, since p53 is the most commonly mutated protein identified in human cancers, the number of antibodies necessary to detect all of the different mutant forms of p53 may be quite high; this method would be impractical and costly. Thirdly, by its very nature the use of p53 antibodies, similar to the DNA sequencing method described above, is performed on cell lysates. It is not applicable to living cells.

Other methods for determining p53 in cells are shown in the following patent applications. EPA 518 650, inventor Vogelstein, B. et al., describes a method for detecting p53 in cellular extracts using DNA sequences that are specific for p53 binding.

WO 94/11533 describes determining the presence of functional p53 in cells by measuring mRNA or protein encoded by a gene termed GADD45, which is an acronym for growth-arrest and DNA-damage inducible gene.

It is important to note that all presently used p53 assays require several days to complete and cannot be performed in vivo. That is, they cannot be performed without surgically biopsing, and lysing the tumor cells.

Considering the importance that tumor suppressor proteins play in regulating cell growth, and those studies that have shown that their absence is involved in establishing the malignant phenotype, methods have been developed to replace tumor suppressors in cancer cells that lack them. The most studied method centers on the delivery of the appropriate tumor suppressor gene to cancer cells using a viral vector. Perhaps the most studied vector is adenovirus. Partly because of this work, a considerable amount of information exists regarding the genetic properties of adenovirus, and how to construct recombinant forms of the virus. See, for example, Horwitz, M. S. Adenoviridae and their Replication, In: Fields, B. N. and Knipe, D. M., eds., Fundamental Virology, 2nd ed. New York, N.Y., Raven Press, Ltd., pages 771–813 (1991); and Jolly, D. Cancer Gene Therapy, vol. 1, pages 51–64 (1994).

Mittal et al., Virus Research, vol. 28, pages 67–90 (1993) shows an adenovirus type 5-luciferase recombinant containing the firefly luciferase gene flanked by simian virus 40 (SV 40) regulatory sequences inserted into the early region 3 of the adenovirus-5 genome.

Quantin et al., Proc. Natl. Acad. Sci. vol. 89: pages 2581–2584 (1992), discloses a recombinant adenovirus containing the beta-galactosidase reporter gene under the control of muscle-specific regulatory sequences. This recombinant virus directs the expression of beta-galactosidase in myotubes in vivo.

Akrigg, A., et al., PCT/GB92/01195, discloses recombinant adenovirus for use in the detection of a trans-acting gene function in a target eukaryotic cell.

As mentioned above, the tumor suppressor protein p53 has recently been implicated as playing a critical role in causing tumor cell death, or apoptosis, induced by radiation or certain chemotherapeutic agents. See, Lowe et al., Cell, vol. 74; pages 957–967 (1993). Thus, it will be appreciated that an assay for p53 is desired that does not have the limitations of currently used assays. In particular, an assay that permits the in vivo diagnosis of the p53 status of tumor cells, or a more rapid method of assaying a tumor biopsy for p53, would greatly aid a physician in selecting the most effective method of ridding a patient of such tumors.

SUMMARY OF THE INVENTION

A first object of the invention is to describe a rapid, preferably in vivo method for determining the status of tumor suppressor proteins in a patient's tumor cells, which method includes contacting the tumor cells with a first and second polynucleotide sequence such that they are taken up by the tumor cells. The first polynucleotide sequence encodes a reporter molecule that is operably linked to the second polynucleotide sequence which sequence binds the tumor suppressor. Binding of the tumor suppressor causes the expression of the reporter molecule, which is detected or quantitated.

A second object of the invention is to describe a method for determining the status of the tumor suppressor protein, p53, in a patient's tumor cells in vivo, which method includes contacting the tumor cells with a first and second polynucleotide sequence such that they are taken up by the tumor cells. The first polynucleotide sequence encodes a reporter molecule that is operably linked to the second polynucleotide sequence which binds p53. Binding of p53 to the second polynucleotide sequence causes the expression of the reporter molecule, which is detected or quantitated.

A third object of the invention is to describe a method, as stated in the first paragraph above, such that contacting tumor cells with the first and second polynucleotide sequences includes using a replication defective virion.

A fourth object of the invention is to describe a composition for use in a method for determining the status of tumor suppressor proteins, and preferably the tumor suppressor, p53, in a patient's tumor, as stated in the second paragraph above, wherein the composition includes a replication defective adeno virus.

A fifth object of the invention is to describe a composition for use in a method as stated in the first paragraph above, such that contacting tumor cells with the first and second polynucleotide sequences includes using a lipid complex such that the polynucleotide sequences are encased within, or associated with lipids, preferably in the form of a liposome.

A sixth object of the invention is to describe methods and compositions for determining the tumor suppressor status of a patient's tumor, and preferably the tumor suppressor p53, in conjunction with other diagnostic methods, including magnetic resonance imaging, histology, and other methods known in the art that are routinely used by oncologists.

A seventh object of the invention is to describe methods and compositions for determining the tumor suppressor status of a patient's tumor, and preferably the tumor suppressor p53 in tumors of the head and neck, wherein the first nucleotide sequence referred to above in paragraph one encodes the reporter molecule, Green Fluorescent Protein.

These and other objects of the invention will become apparent upon a full consideration of the disclosure presented below.

BRIEF DESCRIPTION OF THE FIGURES

FIG. 2 shows the restriction sites of the multiple cloning site (MCS) in the vector pGFP-1.

FIG. 4 shows the vectors pΔE1sp1A or pΔE1sp1B.

DETAILED DESCRIPTION OF THE INVENTION

Figure 1:
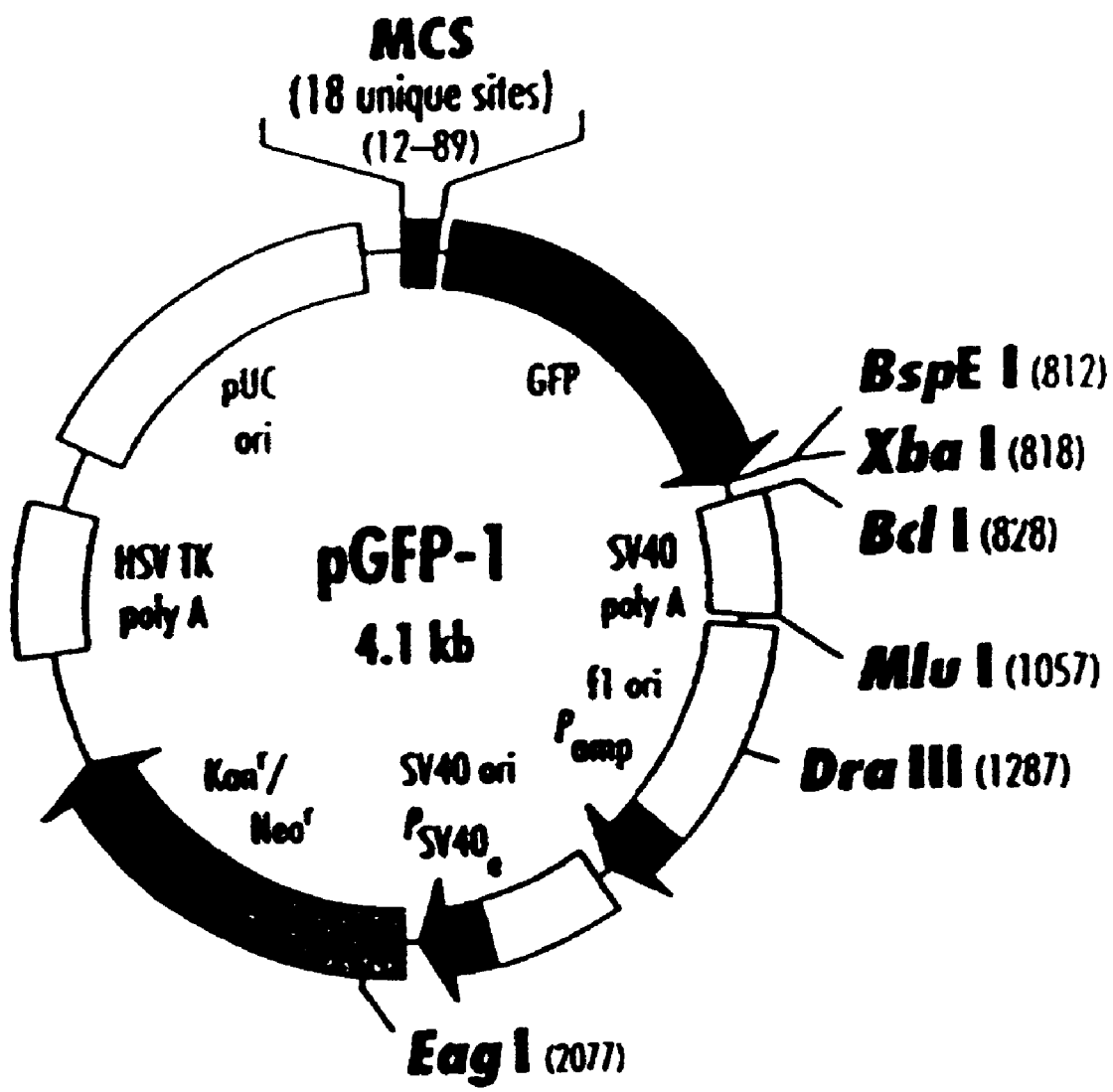
FIG. 1 shows the vector, pGFP-1. Note that the vector contains a multiple cloning site (MCS) upstream of the Green Fluorescent Protein (GFP) coding sequence followed by the simian virus 40 (SV40) polyadenylation signal which facilitates efficient polyadenylation and expression of GFP in mammalian cells.

The references described herein, including scientific publications and patents or patent applications, are intended to be fully incorporated by reference.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al., *Molecular Cloning: A Laboratory Manual,* 2nd. edition (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

In the formulas representing selected specific embodiments of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the polypeptide notation used herein, the lefthand end of the molecule is the amino terminal end and the righthand end is the carboxy-terminal end, in accordance with standard usage and convention. Of course, the basic and acid addition salts including those which are formed at nonphysiological Ph values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid. In keeping with standard polypeptide nomenclature (described in *J. Biol. Chem.* 243:3552–59 (1969) and adopted at 37 CFR §1.822 (b)(2)).

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

Suitable host cells include prokaryotes, yeast cells, or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are DH5a, *E. coli* W3110 (ATCC 27,325), *E coli* B, *E. coli* X1776 (ATCC 31,537) and *E. coli* 294 (ATCC 31,446).

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nucleic Acids Res.* 8, 4057 (1980) and EPO Application Publication Number 36,776) and the tac promoter (H. De Boer et al., *Proc. Natl. Acad. Sci. USA* 80, 21 (1983)). While these are commonly used, other microbial promoters are suitable. Details concerning nucleotide sequences of many promoters have been published, enabling a skilled worker to operably ligate them to DNA in plasmid or viral vectors (Siebenlist et al., *Cell* 20, 269, 1980)). To express eukaryotic genes and prokaryotic genes with a weak ribosome-binding site see Sambrook et al. (1989) "Expression of cloned genes in *Escherichia coli.*" In *Molecular Cloning: A Laboratory Manual*. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter can also be composed of a bacteriophage promoter and an E. coli operator region (EPO Pub. No. 267,851).

Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216, 4,912,040, 4,740,461, and 4,959,455. The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide (s) in liposomes, and direct microinjection of the DNA into nuclei.

Preferred Embodiment of the Invention

The invention described herein is a rapid method for determining the status of a tumor suppressor protein in a patient's tumor cells, preferrably in vivo, which method includes contacting the tumor cells with a first and second polynucleotide sequence such that they are taken up by the tumor cells. The first polynucleotide sequence encodes a reporter molecule that is operably linked to a second tumor suppressor binding polynucleotide sequence. Binding of the tumor suppressor causes the expression of the reporter molecule, which is detected or quantitated.

A key advantage of the instant invention over prior art methods of detecting the presence, or quantifying the amount of a tumor suppressor is that it can be carried out in vivo without biopsing a patient's tumor, or alternatively if the tumor is biopsied the p53 status may be determined rapidly without lysing the tumor cells. In both instances, and therefore in its most practical form involving the use of a first polynucleotide sequence that encodes green fluorescent protein the invention is practiced by illuminating a tumor in vivo, or biopsied tumorous material with the appropriate wavelength of light after an appropriate time after the tumor has incorporated the first and second polynucleotide sequences.

However, it will be appreciated that a physician may wish to use other methods in combination with the invention method, including conventional histochemical techniques on biopsied material, magnetic resonance imaging, and the like, to learn as much about the tumor as possible before recommending a particular treatment regime. For some situations, as discussed more below, a second diagnostic method will facilitate a physician's decision how to best treat a cancer patient. Thus, the invention method is rapidly carried out since a biopsy, and attendant biochemical or molecular biological procedures to detect either the tumor suppressor itself or the gene that encodes it are not required.

A confirmatory biopsy may be particularly desired in those instances where the tumor is determined to have a negative tumor suppressor status. This could be due to the presence of intracellular agents that bind to and inactivate the tumor suppressor, thus making it unavailable for binding to the second tumor suppressor nucleotide binding sequence. An example would include human papilloma virus (HPV), and particularly the protein E6 of the virus. E6 is known to bind tightly to the tumor suppressor p53. Werness, et al., *Science*, vol. 248; page 76 (1990).

By "tumor suppressor" is intended a structural protein, or corresponding fragments or mutations thereof that are effective in reducing or eliminating the transformed or malignant phenotype of certain cancer cells.

In one embodiment of the invention, the tumor suppressor proteins include, but by no means are limited to, p53, retinoblastoma protein (Rb), adenomatous polyposis coli protein (APC), "mutated in colorectal carcinoma protein" (MCC), Wilm's tumor 1 protein (WT1), neurofibromatosis type 1 protein (NF1), or neurofibromatosis type 2 protein (NF2). Thus, it is important to note that while the invention is described with regard to the tumor suppressor p53, it should not be construed as being so limited. It will be appreciated that for each tumor suppressor protein, the appropriate second polynucleotide will be chosen to effect expression of the reporter molecule.

In another embodiment the invention is practiced by incorporating in a target tumor cell population in a patient whose p53 status is sought to be determined a first polynucleotide sequence that encodes a reporter molecule that is operably linked to a second p53 binding polynucleotide sequence. Binding of p53 to the second p53 binding polynucleotide sequence causes the expression of the reporter molecule, which is detected or quantitated as is appropriate for the particular reporter molecule chosen. Additionally, as is known in the art, other polynucleotide sequences may be present that affect the expression of the first and second polynucleotide sequences. Such would include, for example, a suitable polyadenylation sequence which may be the SV40 early polyadenylation sequence.

Certain polynucleotide sequences are known in the art that bind p53 and that can be operably linked to the first polynucleotide sequence that encodes the reporter molecule. See, for example, U.S. Pat. No. 5,362,623 and EPA 518 650, inventor Vogelstein, B. et al. There is described a method for detecting p53 in cellular extracts using DNA sequences that are specific for p53 binding. These p53 polynucleotide binding sequences may be used in the instant invention when put in operable linkage with the second polynucleotide sequence that encodes the reporter molecule.

The first and second polynucleotide sequences may be incorporated in a target tumor cell population by a suitable viral expression vector that carries the sequences, with or without agents that enhance their uptake by the tumor. A variety of viral vectors and methods of making them are known in the art. See, for example, Jolly, D. Cancer Gene Therapy, vol. 1, pages 51–64 (1994). Preferred viral vectors include adenovirus, and papalloma virus. See, for example, Horwitz, M. S. Adenoviridae and their Replication, In: Fields, B. N. and Knipe, D. M., eds., Fundamental Virology, 2nd ed. New York, N.Y., Raven Press, Ltd., pages 771–813 (1991); and Howley, P. M. Papillomavirinae and their Replication, In: Fields, B. N. and Knipe, D. M., eds., Fundamental Virology, 2nd ed. New York, N.Y., Raven Press, Lta., pages 743–767 (1991).

Numerous other virions would perform adequately in the invention, and the materials and methods for making such are well known in the art. The preferred adenovirus is replication defective. See, for example, PCT/US 94/14502, titled "Adenovirus Gene Expression System," inventor Galck-Pedersen, E.; and PCT/US 94/12401, titled "Recombinant p53 Adenovirus Methods and Compositions," inventors Zhang, W. W, et al. More preferred are those replication defective adenovirions in which the E1A and E1B regions of adenovirus have been deleted.

Techniques for preparing replication defective adenovirus are well known in the art, as exemplified by Ghosh-Choudhury and Graham F., Biochem. Biophys. Res. Comm. vol. 147: pages 964–973 (1987); McGrory et al., Virology, vol. 163: pages 614–617 (1988); and PCT/US 94/12401. See also: Graham, F. and Prevec, L. Manipulation of Adenovirus Vectors. In: Methods in Molecular Biology, vol. 7; Gene Transfer and Expression Protocols. Murray E. J. (ed.). The Humana Press Inc., Clifton N.J., Vol. 7: pages 109–128. The desired viral vector can be purified by techniques well known to the skilled practitioner of this art. A preferred means of purification will involve the use of buoyant density gradients, particularly cesium chloride gradient centrifugation.

Suitable expression cassettes can be used to construct replication defective virions of the instant invention. By "expression cassettee" is intended a DNA molecule having a transcription promoter/enhancer, a foreign gene, and in certain instances, a polyadenylation signal. In the context of the instant invention the promoter would be p53 responsive, or that is to say, the second polynucleotide sequence as described herein. The foreign gene, or the first polynucleotide sequence, would be a gene that encodes a suitable reporter molecule that is operably linked to the p53 responsive promoter.

It is also well known that various cell lines may be used to propagate recombinant adenoviruses, so long as they complement any replication defect which may be present. A preferred cell line is the human 293 cell line, but any other cell line that is permissive for replication, i.e., in the preferred case, which expresses E1A and E1B may be employed. Further, the cells can be propagated either on plastic dishes or in suspension culture, in order to obtain virus stocks thereof. The 293 cell line, as well as certain adenovirus vectors can be obtained from Microbix Biosystems, Inc., 341 Bering Avenue, Toronto, Ontario, Canada M8Z 3A8. See also: Graham, F. et al., J. Gen. Virol., vol. 36: pages 59–74 (1977).

The invention is not limited to virus lacking E1 and E1-expressing cells. Indeed, other complementary combinations of viruses and host cells may be employed in connection with the present invention. Virus lacking functional E2 and E2-expressing cells may be used, as may virus lacking functional E4 and E4-expressing cells, and the like. Where a gene which is not essential for replication is deleted and replaced, such as, for example, the E3 gene, this defect will not need to be specifically complemented by the host cell.

The replication defective adenovirus may be of any of the 42 different now serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which there is a significant amount of biochemical and genetic information known, and which has historically been used for most constructions employing adenovirus as a vector.

In addition to viral vectors, the first and second polynucleotide sequences may also be delivered to a target tumor cell mass in a patient using an appropriate plasmid expression vector. Such vectors and methods are known in the art.

Yet another method for delivering the first and second polynucleotide sequences to a patient's tumor is by encasing them within, or associating them with lipids, preferably in the form of a liposome. Liposome transfection can be via liposomes composed of, for example, phosphatidylcholine (PC), phosphatidylserine (PS), cholesterol (Chol), N-[1-(2, 3-dioleyloxy)propyl]-N,N-trimethylammonium chloride (DOTMA), dioleoylphosphatidylethanolamine (DOPE), and/or 3β[N-(N N-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described by Nicolau et al., Methods in Enzymology, vol. 149: pages 157–176 (1987) and Gao et al., Biochemical and Biophysical Research Communications, vol. 179: pages 280–285. Liposomes comprised of DOTMA, such as those which are available commercially under the trademark Lipofectin™, from Vical, Inc. (San Diego, Calif.) may also be used.

Liposomes may be introduced into contact with cells to be transfected by a variety of methods. In cell culture, the liposomes are simply dispersed in the cell culture solution. However, for application in vivo, liposomes are typically injected. Intravenous injection allows liposome-mediated transfer of the polynucleotide sequences to the liver and the spleen. In order to allow transfection of the polynucleotide sequences into tumor cells which are not accessible via injection, the liposome-polynucleotide sequences may be directly injected into a specific location in an patient's body, as discussed more below.

The present invention also contemplates compositions comprising a liposomal complex, and the first and second polynucleotide sequences referred to above. The lipid employed to make the liposomal complex can be any of the above-discussed lipids. In particular, DOTMA, DOPE, and/or DC-Chol may form all or part of the liposomal complex. In a preferred embodiment, the lipid will comprise DC-Chol and DOPE consisting of a ratio of DC-Chol:DOPE between 1:20 and 20:1. More preferred are liposomes prepared from a ratio of DC-Chol:DOPE of about 1:10 to about 1:5.

Liposomes can be used to deliver the first and second polynucleotide sequences by intravenous administration, direct injection into the tumor, or other routes known in the art.

As mentioned above, intravenously injected liposomes are taken up essentially in the liver and the spleen by the macrophages of the reticulendothelial system. The specific site of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, Biol. Cell, vol. 47: pages 121–130 (1983). Thus, liposomes with the invention polynucleotide sequences can effectively be targeted to tumors of the liver and/or spleen that originate in these regions, or to tumors that originate elsewhere and metastasize to these organs.

Intravenous injection is one means of realizing site specific delivery of the liposome/polynucleotide sequences. Such can be delivered selectively to the appropriate target tumor cells by other means, and a preferred means is via a catheter, as described by Nabel et al., Science, vol. 249: pages 1285–1288 (1990). For example, Nabel et al., above, teach injection via a catheter into the arterial wall. Importantly, these methods permit delivering of the liposome/polynucleotide sequences at a specific site in vivo and not just to the liver and spleen cells which are accessible via intravenous injection.

The present invention is practiced by incorporating in a target cell population whose p53 status is sought to be determined a first polynucleotide sequence that encodes a reporter molecule that is operably linked to a second p53 binding polynucleotide sequence. A large number of reporter molecules may be employed in the instant invention that are expressed upon the binding of p53 to the second polynucleotide p53 binding sequence.

The preferred reporter molecule is Green Fluorescent Protein. See, Chalfie, M., et al., Science, vol. 263: pages 802–805. This protein absorbs blue light at 395 nm and emits green light at 509 nm. The fluorescence is stable, and exhibits little or no photobleaching. It has the advantage over other reporter molecules, particularly enzymes, since it does not require a substrate, co-factor or any other protein to be detected. Thus, it is readily detected in a patient merely by exposing the tumor mass to blue light, and observing the emission of green light.

The cDNA that encodes Green Fluorescent Protein has been cloned and expressed in heterologous systems. See Prasher, D. C., et al. (1992) Gene: vol. 111: pages 229–233; and Inoue, S. and Tsuji, F. I.(1994) FEBS Letters, vol. 341: pages 277–280. See also, WO 9507463, inventors Chalfie, M, and Prasher, D. The clone is available from Clontech Laboratories in a number of plasmids, and with a variety of restriction sites that facilitate constructing viral or plasmid expression vectors using it as the reporter molecule.

Other reporter molecules include enzymes which may serve as the means for detecting the presence of p53. These will preferrably be used to determine the status of p53 in tumor biopsies. The enzyme is preferably one that can easily be assayed for or detected in a tumor mass. Enzymes having such utility would generally include hydrolases and oxidoreductases, and exemplary enzymes are β-glucuronidase, β-hexosaminidase, luciferase, phospholipases, and phosphates. It should be noted that Quantin et al., Proc. Natl. Acad. Sci. vol. 89: pages 2581–2584, discloses a recombinant adenovirus containing the beta-galactosidase reporter gene under the control of muscle-specific regulatory sequences. This recombinant virus directs the expression of beta-galactosidase in myotubes in vivo.

Use and Administration

Certain methods of preparing dosage forms of the invention compositions are known, whether the first and second polynucleotide sequences are delivered to a tumor by an appropriate vector (i.e. viral, plasmid, etc.) or in association with lipids (i.e. liposomes) referred to above. See, e.g., Remington's Pharmaceutical Sciences, Mack Publishing Company, Easton, Pa., 17th edition, 1985. The composition or formulation to be administered will, in any event, contain a quantity of the first and second polynucleotide sequences adequate to achieve the desired read out of the reporter molecule in the subject being treated.

The various compositions of the present invention will preferably be used in combination with pharmaceutically acceptable excipient materials. Preferred pharmacologically acceptable excipients include neutral saline solutions buffered with phosphate, lactate, Tris, and other appropriate buffers known in the art.

A typical procedure for determining the tumor suppressor status of a cancer patient's tumor will consist of administering a composition of the first and second polynucleotide sequences to the patient, waiting for an empirically determined period of time so that the composition is delivered to and taken up by the tumor. Next, the presence of the tumor suppressor is determined as dictated by the nature of the reporter group being assayed by biopsying the tumor using standard techniques and performing the appropriate assay.

In those instances where the first and second polynucleotide sequences are administered intravenously to a patient via a viral vector the titers of virus will be in the range of $10^6$–$10^{12}$ plaque forming units (pfu) per ml.

The instant invention will preferrably be employed for a determination of the p53 tumor suppressor status of tumors that are readily detectable without invasive procedures using the reporter molecule, Green Fluorescent Protein. Most preferred will be diagnosing cancers of the head and neck. For example, certain of these types of cancers can be externally injected with adenovirus the carries the first and second polynucleotide sequences, with the first polynucleotide sequence encoding Green Fluorescent Protein. After the virus has infected the tumor cells, the presence of p53 can preferably be determined merely by shinning light of the appropriate wavelength directly on the tumor, and observing if light of the appropriate wavelength attributable to Green Fluorescent Protein is emitted. Green Fluorescent Protein absorbs blue light at 395 nm and emits green light at 509 nm. Alternatively, such tumors could be biopsied and assayed for the emission of green light before or after infection with virus.

The invention is demonstrated by the following examples. However, while these examples are exemplary of the invention, it will be appreciated by those of skill in the art that certain modifications and alterations may be made without departing from the spirit and scope of the invention.

EXAMPLE 1

Construction of Recombinant Replication Defective Adenovirus with First and Second Polynucleotide Sequences One strategy for constructing a recombinant replication defective adenovirus with first and second polynucleotide sequences will consist of constructing a "GFP cassette" consisting of a p53 DNA binding sequence, a "TATA box," the GFP coding sequence, and a polyadenylation sequence, preferably from SV40. The preferred method for generating the cassette is to modify an existing pGFP-1 promoter reporter vector that is available from Clontech (See, Clontechniques, vol. 11, no. 2, April 1996), and which incorporates the GFP coding sequence, and the SV40 polyadenylation sequence. Both the p53 DNA binding sequence, and "TATA box," are cloned into the vector upstream from the GFP coding region and SV40 polyadenylation sequence. This cassettee can be excised from the pGFP-1 promoter reporter vector and cloned into an adenovirus transfer vector that contains the part of the adenovirus genome required for virus packaging and replication. The adenovirus genomic region present in this transfer vector is designed to permit homologous recombination with a plasmid vector containing the remainder of the adenovirus genome after cotransfection in human 293 cells. Co-transfection of these two sets of plasmids, one containing the "GFP cassette" and a part of the adenovirus genome, and the other containing most of the remaining adenovirus genome, into human 293 cells would result in homologous recombination of the two constructs, and yield progeny virus that would contain the "GFP-cassette" in an adenovirus vector suitable for diagnostic use. The virus can be harvested, and purified using standard methods.

More specifically, for efficient expression of GFP in mammalian cells, the "TATA" box element is incorporated into the vector construct. This sequence is synthesized as an oligonucleotide, made double stranded and then cloned in between the p53 DNA binding site and the GFP coding sequence in the Clonetech vector, pGFP-1. FIG. 1 shows the vector, pGFP-1, while FIG. 2 shows the restriction sites of the multiple cloning site (MCS) in the vector.

A preferred TATA-box element is the TATA-box from the adenovirus E1B gene itself. The sequence of this element is described by Lillie and Green, Nature vol. 338, pages 39–44 (1989). The double stranded sequence is made having Kpn 1 and Apa 1 restriction sites to be compatable with such restriction sites in the MCL of the pGFP-1 promoter vector, and the sequence is:

5'-CAGGGTATATAATGGGCC-3' (SEQ ID No. 1)
3'-CATGGTCCCATATATTAC-5'(SEQ ID No. 2)

Thus, the above double stranded TATA-box element is cloned into the pGFP-1 promoter vector that has been digested with the restriction enzymes, Kpn 1 and Apa 1. Upon ligation of the double stranded sequence the resultant vector is termed pGFP-1TATA.

Next, a p53 DNA binding site consensus sequence is synthesized as an oligonucleotide containing appropriate restriction enzyme sites at each end in order to permit cloning of the double-stranded oligonucleotide into the vector pGFP-1TATA.

A p53 binding DNA consensus sequence is:

5'- RRR CAT GYY YRR RCA TGY YY- 3'(SEQ. ID No. 4)

where R=A or G, and Y=C or T.

The preferred p53 DNA binding site sequence is: 5'-AACATGTCCCAACATGTTG- 3'(SEQ ID No. 4)

It is desirable to have multiple such p53 DNA binding site sequences to enhance the expression of GFP. Thus, the p53 DNA binding sequence is made double stranded, and having Hind III restriction sties at both ends, which facilitates multimerization of the sequence. This double stranded sequence is cloned into the pGFP-1TATA vector.

The preferred double-stranded p53-binding site oligonucleotide has the following sequence:

5'-AGCTTGAACATGTCCCAACATGTTGA-3'(SEQ ID No. 5)
3'- ACTTGTACAGGGTTGTACAACTTCGA-5'(SEQ ID No. 6)

Figure 3:
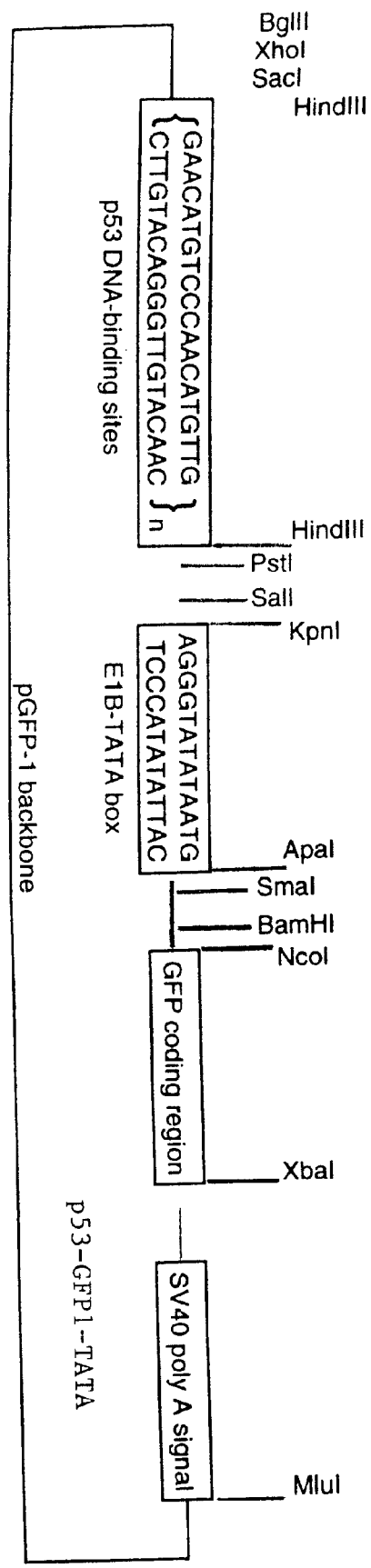
FIG. 3 shows vector p53-GFP1-TATA. This vector is derived from vector pGFP1-TATA by including the p53 DNA binding sequence as shown. Concatomers of this sequence enchance p53 dependent GFP expression.
Figure 5:
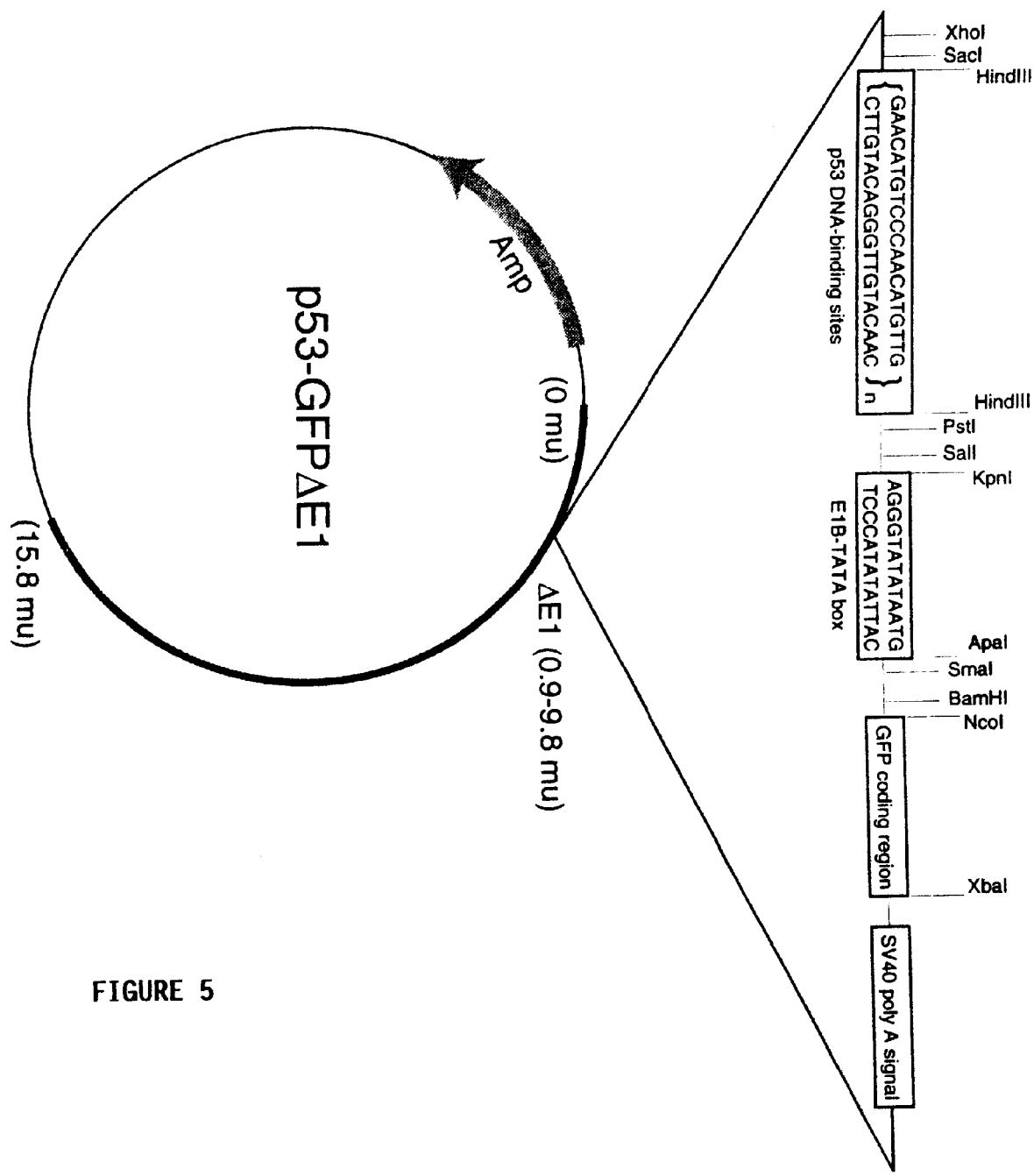
FIG. 5 shows the vector p53-GFPΔE1.

Upon cloning of this double stranded sequence into pGFP-1TATA, concatomers of the p53 DNA binding site are formed to yield a vector termed p53-GFP1-TATA (FIG. 3). By using the appropriate restriction enzymes the "GFP-cassette" present in the vector p53-GFP1-TATA can be excised. This cassette contains the p53-binding site(s), TATA-element, GFP coding region, and the SV40 polyadenylation region. As shown in FIG. 3, the cassette can be excised from p53-GFP1-TATA with the restriction enzymes Bg III and Mlu I, and cloned into the appropriate adenovirus transfer vector, preferrably pΔE1sp1A or pΔE1sp1B. These vectors, pΔE1sp1A or pΔE1sp1B, are shown in FIG. 4, and are described by Bett in PNAS vol. 91, pp 8802, 1994. The resulting plasmid is p53-GFPΔE1sp1A or B (FIG. 5). These plasmid vectors contain the proper left end of the adenovirus genome required for virus packaging and replication, map units 0–0.9 of the adenovirus genome, followed by a MCS (multiple cloning site) where the "GFP-cassette" is cloned into followed by the adenovirus genomic region corresponding to map units 9.8–15.8 in an E. coli shuttle plasmid vector.

The adenovirus genomic region present in this plasmid, p53-GFPΔE1sp1A or B, is designed to permit homologous recombination with a plasmid vector containing the remainder of the adenovirus genome after co-transfection in human 293 cells. The adenovirus genomic plasmid of choice would be pBHG10 or pBHG11 also described by Bett et. al., above. These plasmids contain the adenovirus genome from map units 0–0.5 followed by a deletion of map units from 0.5–3.7, followed by the remainder of the adenovirus genome corresponding to map units 3.7–100 (full adeno genome is 0–100 map units, with each map unit= approximately 360 bp, hence the adeno genome is about 36,000 bp long) in an *E. coli* plasmid shuttle vector. Furthermore, these plasmids contain a deletion of the adenovirus E3 gene region corresponding to 78.3–85.8 map units for pBHG10 and an expanded deletion of the E3 gene region removing sequences from bp 27,865 to 30,995 of the adenovirus genome for pBHG11.

Transfection of these two sets of plasmids, one being the p53-GFPΔE1sp1A or B and the other pBHG10 or pBHG11, together into human 293 cells would result in homologous recombination of the two constructs and yield progeny virus that would contain the "GFP-cassette" in an adenovirus vector for delivery. The virus can then be harvested, and purified using standard methods.

EXAMPLE 2

Incorporation of the First and Second Polynucleotide Sequences into Liposomes Yet another method for delivering the first and second polynucleotide sequences to a patient's tumor is by encasing them within, or associating them with lipids, preferably in the form of a liposome. Liposome transfection can be via liposomes composed of, for example, phosphatidylcholine (PC), phosphatidylserine (PS), cholesterol (Chol), N-[1-(2, 3-dioleyloxy)propyl]-N,N-trimethylammonium chloride (DOTMA), dioleoylphosphatidylethanolamine (DOPE), and/or 3β[N-(N N-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described by Nicolau et al., Methods in Enzymology, vol. 149: pages 157–176 (1987) and Gao et al., Biochemical and Biophysical Research Communications, vol. 179: pages 280–285. Liposomes comprised of DOTMA, such as those which are available commercially under the trademark LIPOFECTIN™, from Vical, Inc. (San Diego, Calif.) may also be used.

Catatonic liposomes are used to effect efficient transfection of the appropriate viral DNA into neoplastic cells and are preferred for use in the instant invention. Such catatonic liposomes can be prepared using the method of Gao et al., Biochemica and Biophysical Research Communications, vol. 179: pages 280–285 (1991), and are a mixture of DC-Chol ("3B(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 umol of DC-Chol and 8.0 umol of DOPE in chloroform. This mixture is then dried, vacuum desiccated, and resuspended in 1 ml sterol 20 mM HEPES buffer (pH 7.8) in a tube. After 24 hours of hydration at 4° C., the dispersion is sonicated for 5–10 minutes in a sonicator to form liposomes with an average diameter of 150–200 nm.

To prepare a liposome/DNA complex, the following steps are followed. Firstly, viral DNA is isolated and purified from adenovirus produced as described in Example 1, and the "GFP-cassette" which contains the p53 consensus binding sequence, TATA-element, GFP coding region, and the SV40 polyadenylation region, is removed with the appropriate restriction enzymes.

The materials and methods for isolating adenovirus, and viral DNA are well known in the art. See, for example, Hitt, M., Bett, A. J., Prevec, L. and Graham, F. L., Construction and propagation of human adenovirus vectors, In: Cell Biology: a Laboratory Handbook; J. Celis (Ed), Academic Press, N.Y. In press; Graham, F. L. and Prevec, L. Manipulation of adenovirus vectors, In: Methods in Molecular Biology, Vol. 7: Gene Transfer and Expression.

Briefly, adenovirus produced as described in Example 1 containing the "GFP-cassette" is grown on the human embryonic kidney cell line HEK293, and the cells infected with the virus at a MOI of 1–10 and incubated until cytopathic effect is visible. The 293 cell line is available from the American Type Culture Collection, # CRL 1573, Rockville, Md.; See also, Graham et al. (1977) *J. Gen. Virol.* 36: 59. The cells are harvested and pelleted by low speed centrifugation. Virus is extracted from the cell pellet by three consecutive freeze/thaw cycles and collected in the supernatant by centrifugation at 10,000 xg for 30 minutes. This crude cell lysate is purified by ultracentrifugation over a series of two CsCl gradients, followed by dialysis against a 500-fold volume of buffer. Aliquots of the purified virus are stored at −70° C. The titer of purified virus is determined by a plaque assay in which HEK293 cells are infected with serially diluted virus, overlaid with growth media containing agarose, and incubated until quantifiable plaques appear on the monolayers. Next, viral plasmid DNA is isolated, purified, and the "GFP-cassette" removed using the appropriate restriction enzymes. The cassette is purified using methods well known in the art, as referred to above.

Finally, the adenoviral "GFP-cassette" DNA is placed in DMEM/F12 medium in a ratio of 15 $\mu$g DNA to 50 $\mu$l DMEM/F12. DMEM/F12 is then used to dilute the DC-Chol/DOPE liposome mixture to a ratio of 50 ul DMEM/F12 to 100 ul liposome. The DNA dilution and the liposome dilution are then gently mixed, and incubated at 37° C. for 10 minutes. Following incubation, the viral DNA/liposome complex is ready for use.

EXAMPLE 3

Determination of the p53 Status of Tumors with Adenovirus Containing the "GFP-cassette"

Experiments are conducted to show that adenovirus containing the "GFP-cassette" is effective to determine the p53 status of tumor cells. Two cell lines are chosen to demonstrate this aspect of the invention. The first, C33A, is a human cervical carcinoma cell line; it is available from the American Type Culture Collection, Rockville Md. The cell line is chosen primarily because it substantially lacks the tumor suppressor protein, p53, and secondly, it grows as a solid tumor. Thus, the cell line can be used as a negative control to show that in the absence of p53 GFP is not expressed. The second cell line, U-87, is p53 positive and also produces tumors. Thus in this cell line GFP will be expressed in the presence of p53. U-87 is also available from the American Type Culture Collection (ATCC HTB-14). Both cell lines are grown under standard cell culture conditions in Dulbecco's Modified Eagles Medium supplemented with Fetal Bovine Serum, amino acids and antibiotics, and passaged at confluency with trypsin.

The experiment is conducted as follows. Female athymic nu/nu nude mice (7–10 weeks old) are given subcutaneous injections into both flanks with either $5 \times 10^6$ C33A or U-87 cells in 0.2 ml of phosphate buffered saline.

The tumors are allowed to grow until they are between 0.15 and 0.40 ml in volume, which generally will take about 1 month. Tumor volume is calculated by multiplying the largest tumor diameter (length) and its perpendicular (width) squared, divided by 2: (length/width$^2$). Next, mice with either tumor are injected with adenovirus containing the "GFP cassette." The injections are subcutaneously into the tumors.

Twenty-four to forty eight hours following injection of the virus into the tumors, the tumors are excised, weighed, measured, and examined histologically for tumor necrosis and infiltration of the tumor by immune effector cells. Portions of the tumor are prepared for histological examination by either frozen sections, or after fixing the sections with formaldehyde. The latter is particularly convenient since GFP fluorescence is not greatly diminished after formaldehyde fixation.

Examination of the slides upon illumination with 450–490 nm light would show that C33A tumors would have little or no GFP fluorescence, whereas sections through U-87 tumors would fluoresce brightly green.

EXAMPLE 4

Liposomal Delivery of "GFP-cassette" Adenovirus DNA to p53+ and p53– Human Tumor Cells Experiments are performed to show that liposomal encapsulation of the DNA from the "GFP-cassette" adenovirus can be used to determine the p53 status of tumor cells in a manner analogous to using the virus. Adenoviral DNA is isolated and encapsulated in catatonic liposomal material as set forth in Example 2. This material is then subcutaneously injected into either C33A or U-87 tumors in nude mice. The procedures for growing the cell lines, and producing and harvesting tumors are as described in Example 3.

The results would show that upon illumination at 450–490 nm of formaldehyde fixed histological sections from C33A and U-87 tumors little or no fluorescence from C33A sections, but bright green fluorescene from U-87 sections, respectively. These results would thus establish that liposomes may be utilized to deliver "GFP-cassette" adenoviral DNA to determine the p53 status of tumor cells in a manner analogous to using the virus.

What are believed to be the preferred embodiments of the invention have been set forth above, nevertheless it will be appreciated by the skilled practitioner of this art that there are other changes and modifications that may be made to the invention without departing from the spirit of the invention and that it is the intent of the inventors to claim all such changes and modifications.

What is claimed is:
1. The plasmid p53-GFPΔE1sp1A.
2. The plasmid p53-GFPΔE1sp1B.
3. A method of producing virus that encodes GFP, comprising
    contacting the plasmid of claim 1 with a cell containing adenoviral genomic sequences to allow for homologous recombination to produce such virus.
4. A method of producing virus that encodes GFP, comprising
    contacting the plasmid of claim 2 with a cell containing adenoviral genomic sequences to allow for homologous recombination to produce such virus.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

CAGGGTATAT AATGGGCC 18

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CATTATATAC CCTGGTAC                                                 18

(2) INFORMATION FOR SEQ ID NO:3:

(i) SEQUENCE CHARACTERISTICS:
             (A) LENGTH: 20 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

RRRCATGYYY RRRCATGYYY                                               20

(2) INFORMATION FOR SEQ ID NO:4:

(i) SEQUENCE CHARACTERISTICS:
             (A) LENGTH: 19 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

AACATGTCCC AACATGTTG                                                19

(2) INFORMATION FOR SEQ ID NO:5:

(i) SEQUENCE CHARACTERISTICS:
             (A) LENGTH: 26 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

AGCTTGAACA TGTCCCAACA TGTTGA                                        26

(2) INFORMATION FOR SEQ ID NO:6:

(i) SEQUENCE CHARACTERISTICS:
             (A) LENGTH: 26 base pairs
             (B) TYPE: nucleic acid
             (C) STRANDEDNESS: double
             (D) TOPOLOGY: linear (ii) MOLECULE TYPE: cDNA (iii) HYPOTHETICAL: NO -continued (iv) ANTI-SENSE: NO (xi) SEQUENCE DESCRIPTION: SEQ ID NO:6:

AGCTTCAACA TGTTGGGACA TGTTCA  26